(12) United States Patent
Boltanski

(10) Patent No.: US 9,431,887 B2
(45) Date of Patent: Aug. 30, 2016

(54) LENS POSITIONING SYSTEM

(71) Applicant: Align Technology, Inc., San Jose, CA (US)

(72) Inventor: Rami Boltanski, Kiryat Ono (IL)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 14/298,648

(22) Filed: Jun. 6, 2014

(65) Prior Publication Data

US 2015/0351879 A1 Dec. 10, 2015

(51) Int. Cl.
| | |
|---|---|
| A61B 1/04 | (2006.01) |
| H02K 41/035 | (2006.01) |
| A61B 1/00 | (2006.01) |
| A61C 9/00 | (2006.01) |
| G02B 7/02 | (2006.01) |
| G02B 7/08 | (2006.01) |
| A61B 1/002 | (2006.01) |
| A61B 1/24 | (2006.01) |

(52) U.S. Cl.
CPC ........... *H02K 41/0356* (2013.01); *A61B 1/002* (2013.01); *A61B 1/00172* (2013.01); *A61B 1/00188* (2013.01); *A61B 1/24* (2013.01); *A61C 9/0053* (2013.01); *A61C 9/0066* (2013.01); *G02B 7/023* (2013.01); *G02B 7/08* (2013.01)

(58) Field of Classification Search
USPC ...................... 396/16, 17, 133; 600/114, 117; 310/12.01, 12.03, 12.16, 14
See application file for complete search history.

(56) References Cited

U.S. PATENT DOCUMENTS

| | | | |
|---|---|---|---|
| 4,482,986 A | 11/1984 | Noda et al. | |
| 4,660,190 A | 4/1987 | Fujit et al. | |
| 4,700,693 A * | 10/1987 | Lia et al. | 600/141 |
| 5,138,497 A * | 8/1992 | Blanding | 359/823 |
| 5,177,640 A * | 1/1993 | Grassens | 359/814 |
| 5,313,332 A * | 5/1994 | Schell et al. | 359/813 |
| 5,442,606 A * | 8/1995 | McCaslin et al. | 369/44.15 |
| 5,762,995 A * | 6/1998 | Kondo et al. | 427/2.12 |
| 6,464,697 B1 * | 10/2002 | Edwards et al. | 606/41 |
| 6,791,669 B2 * | 9/2004 | Poon | 355/72 |
| 7,288,861 B1 * | 10/2007 | Willard et al. | 310/15 |
| 7,824,763 B2 | 11/2010 | Namburi et al. | |
| 7,859,144 B1 * | 12/2010 | Sahyoun | 310/15 |
| 8,254,045 B1 | 8/2012 | Benner, Jr. | |
| 8,415,838 B1 * | 4/2013 | Eghbal et al. | 310/12.16 |
| 2005/0057101 A1 | 3/2005 | Nakagawa et al. | |

(Continued)

FOREIGN PATENT DOCUMENTS

DE 29705315 U1 7/1997

OTHER PUBLICATIONS

International Search Report and Written Opinion for PCT Application No. PCT/IB2015/000836 mailed Nov. 18, 2015.

*Primary Examiner* — David Gray
*Assistant Examiner* — Warren K Fenwick
(74) *Attorney, Agent, or Firm* — Lowenstein Sandler LLP

(57) ABSTRACT

An actuator includes an inner element coupled to an outer element by a linear-motion bearing that provides a single degree of translational movement of the inner element with respect to the outer element along a longitudinal axis. The inner element includes a permanent magnet and the outer element includes a conductive winding with a first coil wound in first direction around a first pole of the permanent magnet and a second coil wound in a second direction around a second pole of the permanent magnet.

29 Claims, 9 Drawing Sheets

(56) References Cited

U.S. PATENT DOCUMENTS

| | | | |
|---|---|---|---|
| 2005/0249487 A1* | 11/2005 | Gutierrez | 396/85 |
| 2008/0180820 A1 | 7/2008 | Sata | |
| 2010/0033835 A1* | 2/2010 | Heim et al. | 359/683 |
| 2011/0210690 A1* | 9/2011 | Vogel | 318/631 |
| 2012/0195551 A1* | 8/2012 | Pezeshki et al. | 385/33 |
| 2013/0136438 A1 | 5/2013 | Lee et al. | |

\* cited by examiner

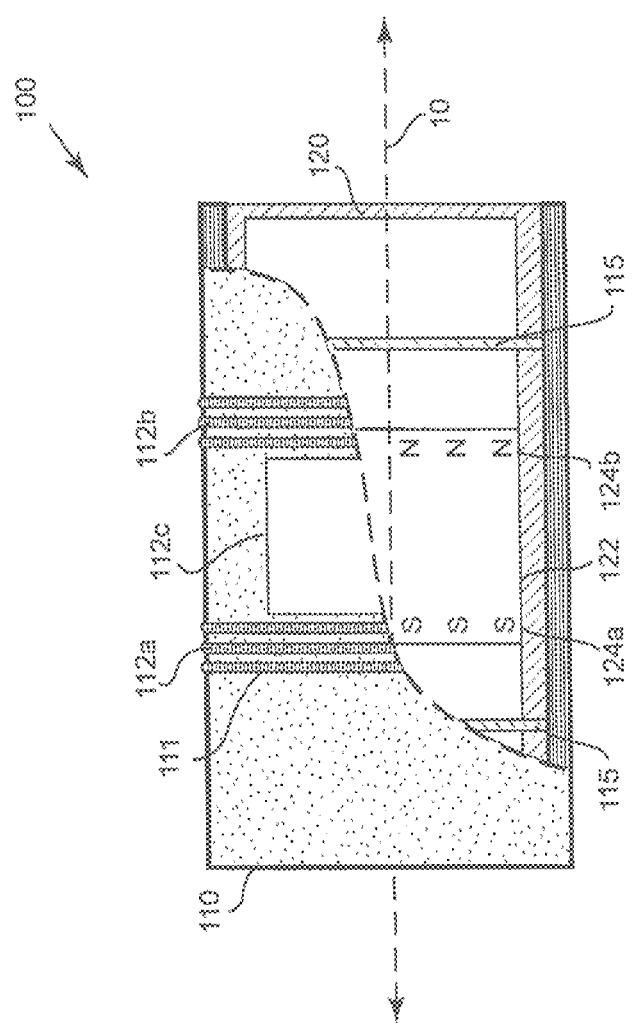

LENS POSITIONING SYSTEM

TECHNICAL FIELD

Embodiments of the present invention relate to the field of linear actuators and, in particular, to a system and method for positioning a lens using a linear actuator.

BACKGROUND

In prosthodontic procedures designed to implant a dental prosthesis in the oral cavity, the dental site at which the prosthesis is to be implanted may be measured accurately and studied carefully, so that a prosthesis such as a crown, denture or bridge, for example, can be properly designed and dimensioned to fit in place. A good fit, for example, enables mechanical stresses to be properly transmitted between the prosthesis and the jaw and minimizes infection of the gums via the interface between the prosthesis and the dental site.

Some procedures call for removable prosthetics to be fabricated to replace one or more missing teeth, such as a partial or full denture, in which case the surface contours of the areas where the teeth are missing may be reproduced accurately so that the resulting prosthetic fits over the edentulous region with even pressure on the soft tissues.

In some practices, the dental site is prepared by a dental practitioner, and a positive physical model of the dental site is constructed. Alternatively, the dental site may be scanned to provide three-dimensional (3D) data of the dental site. In either case, the virtual or real model of the dental site may be sent to a dental lab that manufactures the prosthesis based on the model. However, if the model is deficient or undefined in certain areas, or if the preparation was not optimally configured for receiving the prosthesis, the design of the prosthesis may be less than optimal. For example, if the insertion path implied by the preparation for a closely-fitting coping would result in the prosthesis colliding with adjacent teeth, the coping geometry may be altered to avoid the collision. Further, if the area of the preparation containing a finish line lacks definition, it may not be possible to properly determine the finish line and thus the lower edge of the coping may not be properly designed. Indeed, in some circumstances, the model is rejected and the dental practitioner then re-scans the dental site, or reworks the preparation, so that a suitable prosthesis may be produced.

In orthodontic procedures, it can be important to provide a model of one or both jaws. Where such orthodontic procedures are designed virtually, a virtual model of the oral cavity is also beneficial. Such a virtual model may be obtained by scanning the oral cavity directly, or by producing a physical model of the dentition, and then scanning the model with a suitable scanner.

Thus, in both prosthodontic and orthodontic procedures, obtaining a 3D model of a dental site in the oral cavity may be an initial procedure that is performed. When the 3D model is a virtual model, the more complete and accurate the scans of the dental site are, the higher the quality of the virtual model, and thus the greater the ability to design an optimal prosthesis or orthodontic treatment appliance.

BRIEF DESCRIPTION OF THE DRAWINGS

The present invention is illustrated by way of example, and not by way of limitation, in the figures of the accompanying drawings.

FIG. 4 illustrates a partially cutaway side view of an actuator according to one embodiment.

DETAILED DESCRIPTION

Described herein is a method and apparatus for positioning an object, such as a lens of a scanner. A positioning system includes a controller coupled to an actuator. The actuator includes an inner element coupled to an outer element by a linear-motion bearing that provides a single degree of translational movement of the inner element with respect to the outer element along a longitudinal axis. The inner element may contain a lens, and the longitudinal direction may correspond to (e.g., be parallel to) an axis of the lens. The inner element includes a permanent magnet and the outer element includes a conductive winding. The outer element may include a first coil wound in first direction around a hollow body that houses the inner element at a first end of the permanent magnet and a second coil wound in a second direction around the hollow body that houses the inner element at a second end of the permanent magnet.

A current driven through the conductive winding generates a magnetic field that interacts with the magnetic field generated by the permanent magnet to produce a force that moves the inner element in the longitudinal direction with respect to the outer element while the linear-motion bearing prevents the inner element from moving in other directions. For example, the linear-motion bearing may enable the inner element to move along the axis of a lens in the inner element, while keeping the element from shifting normal to the lens axis (e.g., while keeping the lens axis centered).

Figure 1:
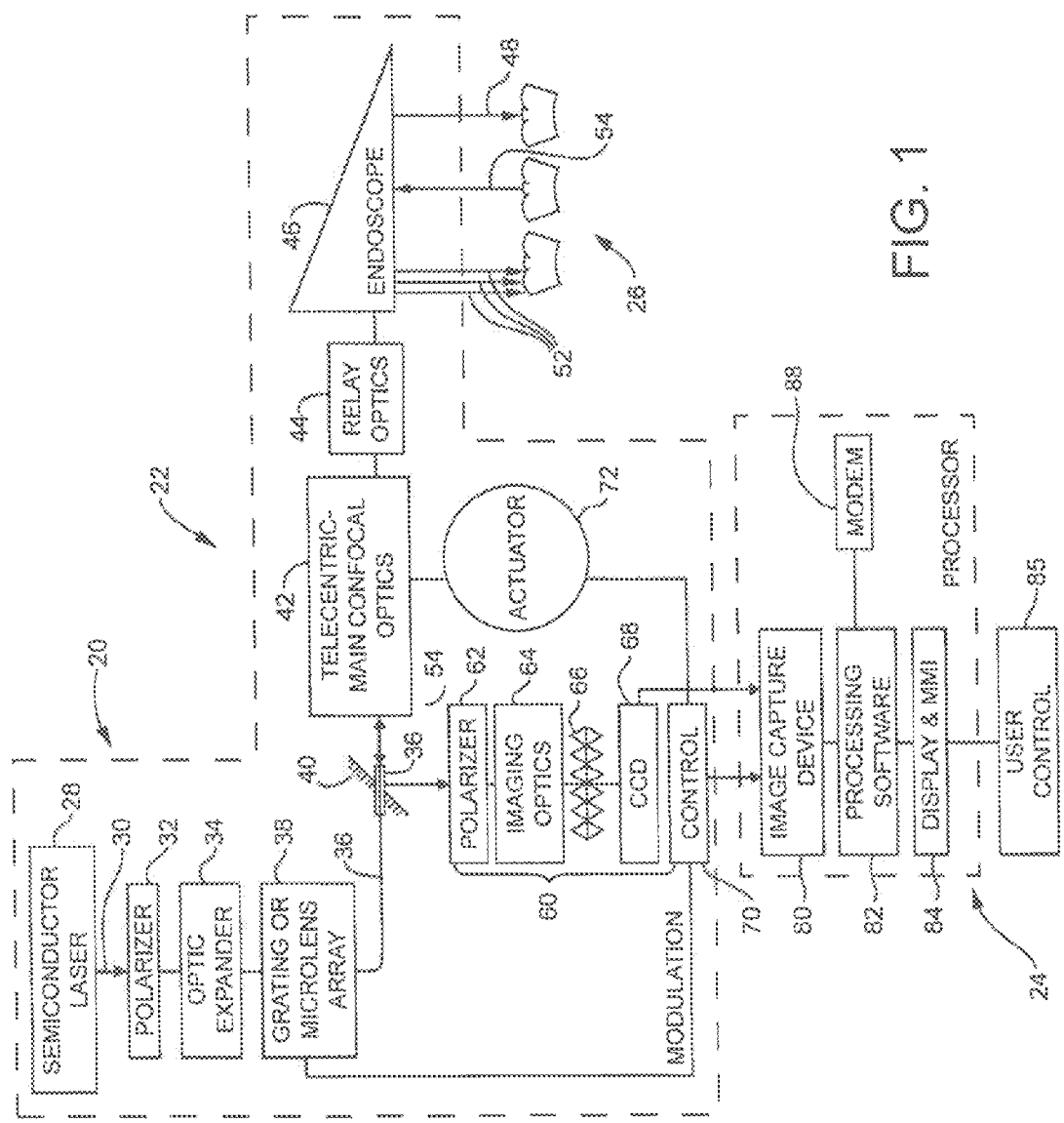
FIG. 1 illustrates a functional block diagram of an optical device according to one embodiment.

FIG. 1 illustrates a functional block diagram of an optical device 22 according to one embodiment. The optical device 22 may be a scanner, such as an intraoral scanner. The optical device 22 includes a semiconductor laser 28 that emits a laser light (represented by the arrow 30). The light passes through a polarizer 32 which gives rise to a certain polarization of the light passing through polarizer 32. The light then enters into an optic expander 34 which improves the numerical aperture of the light beam 30. The light then passes through a module 38 (e.g., a grating or a micro lens array) that splits the parent beam 30 into multiple incident light beams 36, represented in FIG. 1 by a single line for ease of illustration.

The optical device 22 further includes a partially transparent mirror 40 having a small central aperture. The mirror 40 allows transfer of light from the laser source through the downstream optics, but reflects light travelling in the opposite direction. In other embodiments, rather than a partially transparent mirror, other optical components with a similar function may also be used, e.g. a beam splitter. The aperture in the mirror 40 improves the measurement accuracy of the apparatus. As a result of this mirror 40, the light beams will yield a light annulus on the illuminated area of the imaged object as long as the area is not in focus and the annulus will turn into a completely illuminated spot once in focus.

The optical device 22 further includes confocal optics 42 operating in a telecentric mode, relay optics 44, and an endoscope 46. In one embodiment, telecentric confocal optics avoid distance-introduced magnification changes and maintains the same magnification of the image over a wide range of distances in the Z direction (the Z direction being the direction of beam propagation, also referred to as the Z axis or lens axis). The relay optics 44 allow maintenance of a certain numerical aperture of the beam's propagation.

The endoscope 46 typically includes a rigid, light-transmitting medium. The rigid, light-transmitting medium may be a hollow object defining within it a light transmission path or an object made of a light transmitting material (e.g., a glass body or tube). At its end, the endoscope typically includes a mirror of the kind ensuring a total internal reflection. The mirror may direct incident light beams towards a teeth segment 26 that is being scanned. The endoscope 46 thus emits multiple incident light beams 48 impinging on to the surface of the teeth segment 26.

The incident light beams 48 form an array of light beams arranged in an X-Y plane propagating along the Z-axis. If the surface on which the incident light beams hit is an uneven surface, illuminated spots 52 are displaced from one another along the Z-axis, at different (Xi, Yi) locations. Thus, while a spot at one location may be in focus of the optical element 42, spots at other locations may be out-of-focus. Therefore, the light intensity of the returned light beams (see below) of the focused spots will be at its peak, while the light intensity at other spots will be off peak. Thus, for each illuminated spot, multiple measurements of light intensity are made at different positions along the Z-axis. For each of such (Xi, Yi) location, typically the derivative of the intensity over distance (Z) will be made, the $Z_i$ yielding maximum derivative, $Z_0$, will be the in-focus distance. As pointed out above, where, as a result of use of the partially transparent mirror 40, the incident light forms a light disk on the surface when out of focus and a complete light spot only when in focus, the distance derivative will be larger when approaching in-focus position thus increasing accuracy of the measurement.

The light scattered from each of the light spots includes a beam travelling initially in the Z-axis along the opposite direction of the optical path traveled by the incident light beams. Each returned light beam 54 corresponds to one of the incident light beams 36. Given the unsymmetrical properties of the mirror 40, the returned light beams are reflected in the direction of the detection optics 60. The detection optics 60 include a polarizer 62 that has a plane of preferred polarization oriented normal to the plane polarization of polarizer 32. The returned polarized light beam 54 pass through an imaging optic 64, typically one or more lenses, and then through a matrix 66 including an array of pinholes. A CCD (charge-coupled device) camera 68 has a matrix of sensing elements each representing a pixel of the image and each one corresponding to one pinhole in the array 66.

The CCD camera 68 is connected to the image-capturing module 80 of processor unit 24. Thus, each light intensity measured in each of the sensing elements of the CCD camera 68 is received and analyzed by a processor 24.

The optical device 22 further includes a control module 70 connected to a controlling operation of both the semiconductor laser 28 and an actuator 72. The actuator 72 is linked to the telecentric confocal optics 42 to change the relative location of the focal plane of the confocal optics 42 along the Z-axis. In a single sequence of operation, the control unit 70 induces the actuator 72 to displace the confocal optics 42 to change the focal plane location and then, after receipt of a feedback that the location has changed, the control module 70 will induce the laser 28 to generate a light pulse. At the same time, the control module 70 will synchronize the image capturing module 80 to grab data representative of the light intensity from each of the sensing elements of the CCD camera 68. Then, in subsequent sequences the focal plane will change in the same manner and the data capturing will continue over a wide focal range.

The image capturing device 80 is connected to processing software 82 which then determines the relative intensity in each pixel over the entire range of focal planes of optics 42, 44. As explained above, once a certain light spot is in focus, the measured intensity will be maximal. Thus, by determining the $Z_i$, corresponding to the maximal light intensity or by determining the maximum displacement derivative of the light intensity, for each pixel, the relative position of each light spot along the Z-axis can be determined.

Thus, data representative of the three-dimensional pattern of a surface in the teeth segment can be obtained. This three-dimensional representation may be displayed on a display 84 and manipulated for viewing, e.g. viewing from different angles, zooming-in or out, by a user control module 86 (e.g., a computer keyboard, touchpad, mouse, etc.). In addition, the data representative of the surface topology may be transmitted through an appropriate data port, e.g. a modem 88, through any communication network (e.g., a local area network (LAN), wide area network (WAN), public network such as the Internet, etc.) to a recipient.

Figure 2:
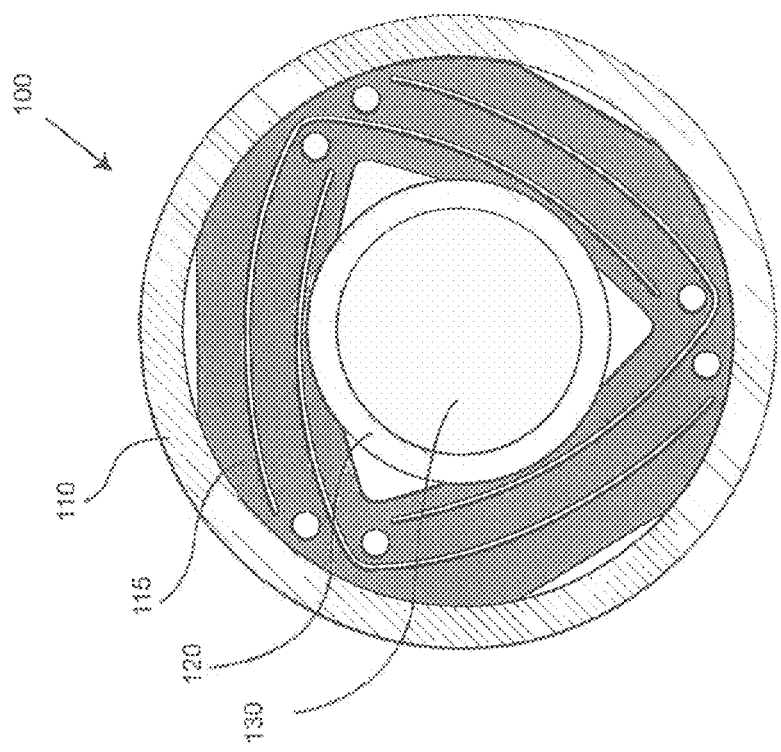
FIG. 2 illustrates an axial view of an actuator according to one embodiment.

FIG. 2 illustrates an axial view of an actuator 100 according to one embodiment. The actuator 100 may be used in place of or may correspond to the actuator 72 of FIG. 1. The actuator 100 includes an inner element 120 that may be moved linearly along a longitudinal axis (into and out of the page) with respect to an outer element 110. The inner element 120 is coupled to the outer element 110 by one or more element couplings 115. The element couplings 115 are deformable to allow the inner element 120 to move with respect to the outer element 110 along the longitudinal axis. The inner element 120 may be concentric with the outer element 110. In one embodiment, the element couplings 115 are leaf spring units.

The inner element 120 may be coupled to one or more components (e.g., a lens) of a telocentric main confocal optics module (e.g., telocentric main confocal optics 42 of FIG. 1). A lens axis of such a lens and/or other components coupled to the inner element 120 may be the Z-axis described with reference to FIG. 1, and may correspond to the longitudinal axis. The inner element 120 and outer element 110 may be concentric with the lens.

The outer element 110 is disposed concentrically around (as viewed in the perspective of FIG. 2) the inner element 120. Although the inner element 120 and outer element 110 of the actuator 100 are illustrated in FIG. 2 as being generally circular, the inner element 120 and outer element 110 may be any shape. Further, although the inner element 120 and outer element 110 are illustrated as being the same shape in FIG. 2, in some embodiments, they may be differently shaped. For example, the inner element 120 may be circular and the outer element 110 may be square or octagonal. The inner element 120 and outer element 110 may be made of metal, plastic, or any other rigid material.

Figure 3:
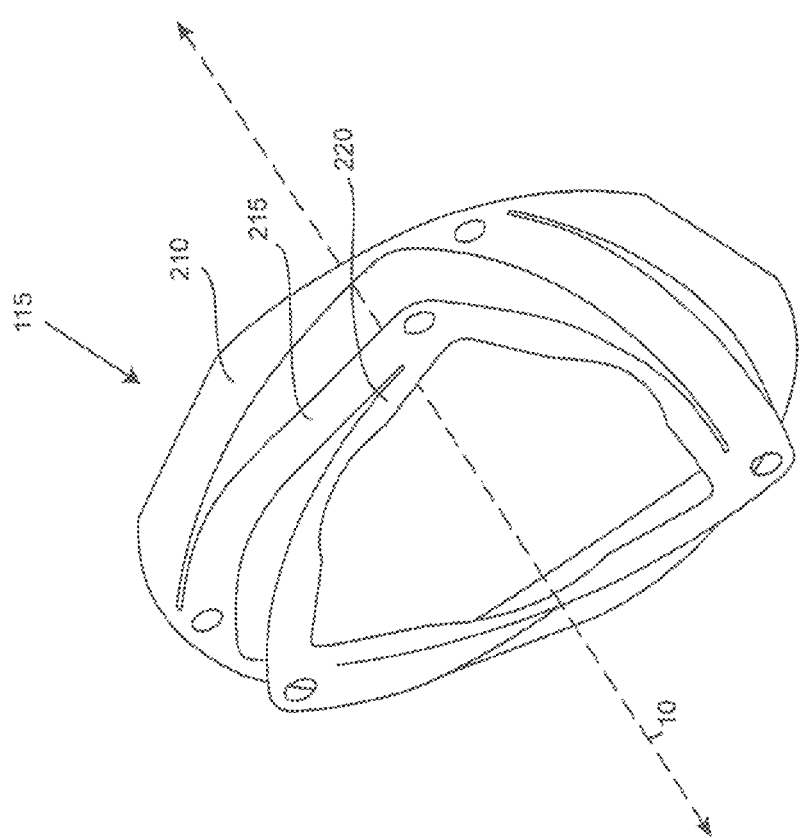
FIG. 3 illustrates a perspective view of an element coupling according to one embodiment.

FIG. 3 is a perspective view of an element coupling 115 (e.g., a leaf spring unit) according to one embodiment. The element coupling 115 of FIG. 3 includes an inner element region 220 that is fixed to the inner element 120 and an outer element region 210 that is fixed to the outer element 110. The inner element region 220 may be an inner mounting ring and the outer element region 220 may be an outer mounting ring. The inner element region 220 and outer element region 210 are connected by three flexures 215 (e.g., leaf spring elements). In other embodiments, the element coupling 115 may have more or fewer flexures 215.

The element couplings 115 (e.g., leaf spring units) may have rotational symmetry with respect to the longitudinal axis, and may be mounted orthogonal to the rotational axis. As the inner element 120 moves with respect to the outer element 110, the flexures 215 bend. The flexures 215 work together to provide a single degree of translational movement along the longitudinal axis 10 of the actuator 100. The flexures 215 similarly work together to prevent any translational movement normal to the longitudinal axis 10. In one embodiment, the element coupling 115 is a single homogenous and contiguous piece of material (e.g., metal) as may be stamped out of a sheet. In another embodiment, the element coupling 115 is made of out multiple pieces. The multiple pieces may all be the same material, or may be composed of different materials.

Each flexure 215 is a gently curved strip of material connected at one end to the inner element region 220 and at the opposite end to the outer element region 210. A curved strip may provide a long enough flexure to allow longitudinal motion while still providing an open center for the lens. In another embodiment, each flexure is a straight strip of material. A straight strip of material may not twist while it bends. In one embodiment, each flexure 215 is a leaf spring. The flexures 215 are oriented in a rotationally symmetric pattern about the longitudinal axis 10, each flexure 215 being substantially perpendicular to a radial axis radiating from the longitudinal axis 10 and/or perpendicular to a line in the direction of the longitudinal axis 10, such that the three flexures 215 generally encircle, circumscribe, or surround the inner element region 220. Such symmetry may provide an actuator 110 that is resistant to thermal drift. That is, changes in temperature may not cause motion of the inner element 120 with respect to the outer element 110.

In an embodiment of an actuator 100 including multiple element couplings such as the element coupling 115 illustrated in FIG. 3, the element couplings 115 may be disposed such that the rotational symmetries are in the same direction (e.g., clockwise or anticlockwise) when viewed from the same end of the longitudinal axis (e.g., the perspective of FIG. 2). Thus, a first inner element region of a first element coupling and a second inner element region of a second element coupling rotate in the same direction as the inner element 120 is moved in the longitudinal direction with respect to the outer element 110. Similarly, the inner element 120 may rotate slightly with respect to the outer element 110 as the inner element 120 moves along the longitudinal axis. Rotation of the inner element 120 will not affect optics due to rotational symmetry. At least two of the element couplings 115, when used together, form a linear-motion bearing between the outer element 110 and the inner element 120.

Although FIG. 3 illustrates an element coupling 115 according to one embodiment, the actuator 100 may include other types of element couplings 115. For example, the element couplings may be other types of linear bearings such as a ball slide, dovetail slide, fluid bearings, roller slide, and so forth. The element couplings may be a thin membrane of a flexible material (e.g., rubber) coupled at its outer edge to the outer element 110 and through which the inner element 120 is inserted. The element coupling 115 of FIG. 3 may provide advantages over other element couplings in that it is substantially friction free, clearance free, and resistant to thermal drift.

As shown in FIG. 2, the inner element 120 houses a lens assembly 130, which may include one or more simple lenses. For example, in one embodiment, the lens assembly 130 may include two optical glass lenses. The lens axis of the lens assembly 130 defines the longitudinal axis of the actuator 100 and the direction of motion along which the actuator 100 moves the lens assembly 130 (by moving the inner element 120 with respect to the outer element 110). The lens assembly 130 may by coupled to the inner element 120 of the actuator 100 by a lens coupling or the lens assembly 130 may be mechanically fitted into the inner element 120.

As noted above, the inner element 120 may be moved with respect to the outer element 110. This motion can be caused in any of a number of ways, such as electromagnetism, pneumatics, electrostatics, and so forth. FIG. 4 illustrates a partially cutaway side view of the actuator 100 of FIG. 2 in which electromagnetism is used to move the inner element 120 with respect to the outer element 110.

Motion of the inner element 120 with respect to the outer element 110 is caused by a force generated by interacting magnetic fields. In one embodiment, the inner element 120 includes a permanent magnet 122 which is ring-shaped around the longitudinal axis 10. In other embodiments, the permanent magnet 122 may include more than one permanent magnets and/or one or more electromagnets. The permanent magnet 122 includes a first end 124a associated with one magnetic pole and a second end 124b associated with the other magnetic pole. The magnetic poles define a magnetic axis that is parallel to the longitudinal axis 10, the axis of motion.

The outer element 110 includes a conductive winding 111 through which a current may be induced by a controller. The conductive winding 111 includes a first coil 112a wound in one direction around the longitudinal axis (e.g., clockwise), a second coil 112b wound in the opposite direction around the longitudinal axis (e.g., counterclockwise), and a connector 112c connecting the first coil 112a and the second coil 112b. The first coil 112a may be in series with the second coil 112b.

The first coil 112a surrounds the first end 124a of the permanent magnet 122. Similarly, the second coil 112b surrounds the second end 124b of the permanent magnet 122. Thus, when a current is driven through the conductive winding 111, a magnetic field is generated in each of the coils 112a, 112b that interacts with the magnetic field generated by the permanent magnet 122. Over a short range of motion, this interaction generates a force that moves the inner element 120 linearly, in the longitudinal direction, with respect to the outer element 110. When current is driven in one direction through the conductive winding 111, the force moves the inner element 120 towards one end of the actuator 100 and when current is driven in the opposite direction through the conductive winding 111, the force moves the inner element 120 toward the opposite end of the actuator 100.

Figure 5:
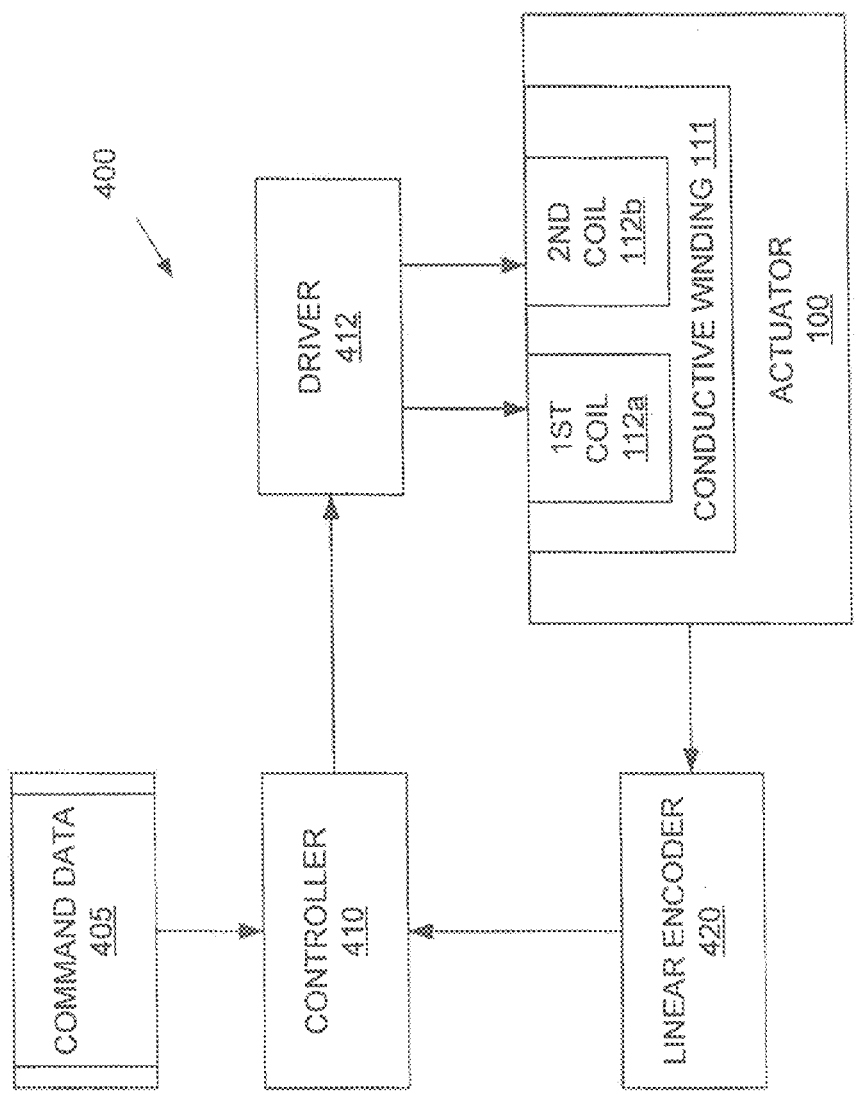
FIG. 5 illustrates a functional block diagram of a positioning system according to one embodiment.

FIG. 5 illustrates a functional block diagram of a positioning system 400. In one embodiment, the positioning system 400 includes the actuator 100 of FIG. 2. In another embodiment, the positioning system 400 includes a different actuator. The positioning system 400 includes a controller 410 that receives command data 405 indicative of desired position of an object (e.g., the lens assembly 130 of FIG. 2). The controller 410 also receives position data from a linear encoder 420 indicative of current position of the object. In particular, the linear encoder 420 provides a measure of the relative position (along the longitudinal axis) of the inner element 120 with respect to the outer element 110. In one embodiment, the linear encoder 420 includes a sensor and a scale. The scale may be mounted upon the inner element 120 of the actuator 100 and the sensor may be mounted upon the outer element 110 of the actuator 100. The linear encoder 420 may be any technology, including optical, magnetic, inductive, capacitive, and eddy current technologies.

Based on the command data 405 and the position data from the linear encoder 420, the controller 410 induces a current by instructing a driver 412 to drive a current through a component of an actuator 100. As described above, the actuator 100 includes, among other components, a conductive winding 111 that includes a first coil 112a wound in one direction and a second coil 112b wound in the opposite direction. Thus, in one embodiment, the controller 410 instructs the driver 412 to drive a current through a first coil 112a wound in a first direction and a second coil 112b wound in a second direction. In one embodiment, the driver 412 drives both coils with a single current (as the coils are connected with a connector 112c). In another embodiment, the driver 412 drives each coil individually with a separate current which may be the same or different.

The driver 412 can receive, as an input, electronic data (which may be analog or digital) indicative of a strength of a current or voltage level and provides, on an output, a current of the indicated strength or a voltage of the indicated level. Although the driver 412 is illustrated as a separate component in FIG. 5, in one embodiment, the controller 410 and the driver 412 may be a single component. In another embodiment, the driver 412 is a part of the actuator 100.

Figure 6:
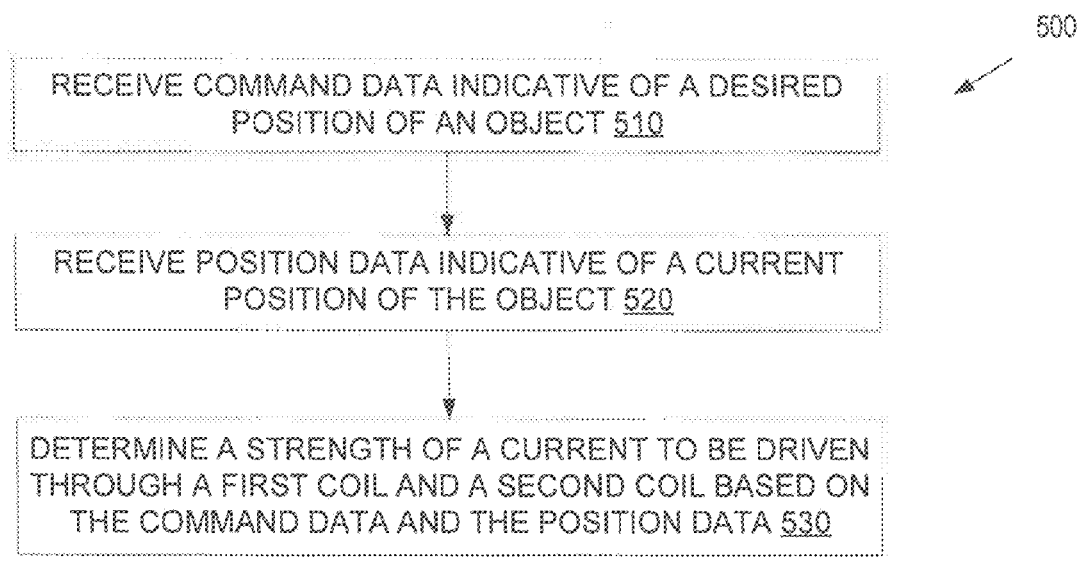
FIG. 6 illustrates a flowchart of a method of positioning an object according to one embodiment.

FIG. 6 illustrates a flowchart of a method of positioning an object according to one embodiment. The method 500 may be performed by processing logic that may include hardware (e.g., circuitry, dedicated logic, programmable logic, microcode, etc.), software (e.g., instructions executed by a processing device), firmware or a combination thereof. For example, the method 500 may be performed by the controller 410 of FIG. 5.

In block 510, the processing logic receives command data indicative of a desired position of an object. The command data may indicate an absolute desired position of the object or communicate that the object is to be moved in a particular direction generally or a particular amount.

In block 520, the processing logic receives position data indicative of the current position of the object. The position data may be received from a linear encoder that senses the position the object. The position data may be received from another source. In one embodiment, the position data is received from the same source as the command data.

In block 530, the processing logic determines, based on the command data and the position data, a strength of a current to be driven through a first coil and a second coil. In one embodiment, the first coil is wound in a first direction around a first pole of a permanent magnet and the second coil is wound in a second direction around a second pole of the permanent magnet. In one embodiment, a voltage level is determined rather than a current strength, the two being interchangeable via Ohm's law (which states that voltage is proportional to current, the proportionality constant being deemed the resistance). In one embodiment, the current to be driven is a direct current. In one embodiment, the current is a non-zero current. In particular, in one embodiment, the current is a non-zero current even when the current position is equal to the desired position.

In the embodiment of FIG. 4, the outer element 110 includes the coils 112a, 112b and the inner element 120 includes the permanent magnet 122. In an alternative embodiment, the position of the coils 112a, 112b and the permanent magnet 122 may be switched such that the inner element 120 includes the coils 112a, 112b and the outer element 110 includes the permanent magnet 122. Such an embodiment is illustrated in FIG. 7.

Figure 7:
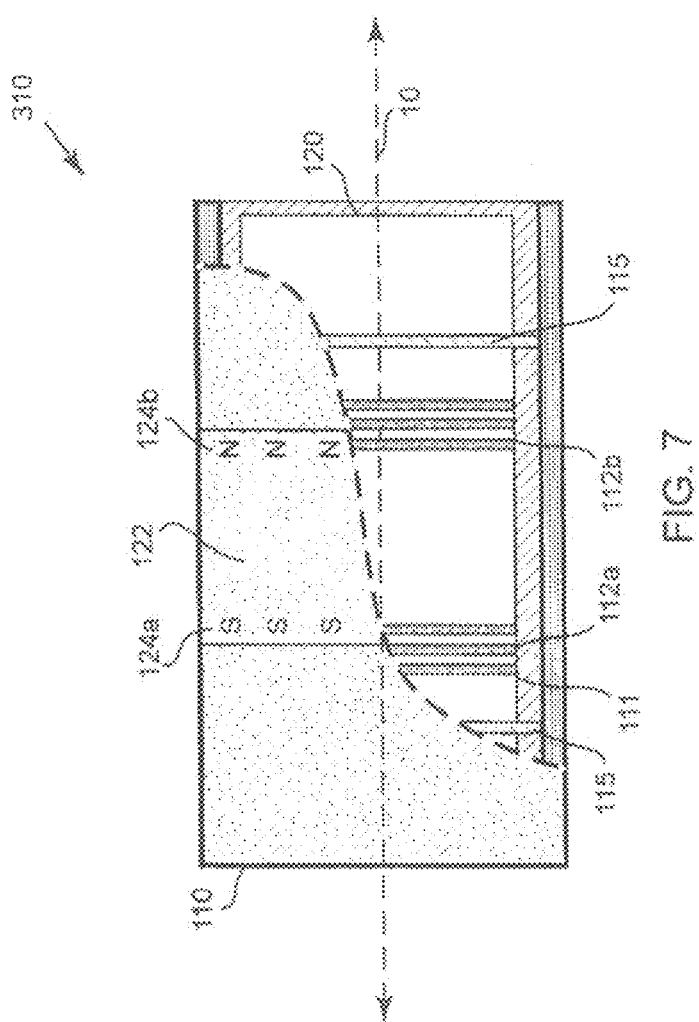
FIG. 7 illustrates a partially cutaway side view of an actuator according to one embodiment.

FIG. 7 illustrates a partially cutaway side view of an actuator 310 according to one embodiment. The actuator 310 is similar to the actuator 100 of FIG. 4 and may be used in similar applications (e.g., the optical device 22 of FIG. 1 or the positioning system 400 of FIG. 5). The actuator 310, like the actuator 100 of FIG. 4, includes an inner element 120 surrounded by an outer element 110 and coupled to the outer element 110 by one or more element couplings 115.

The actuator 310 includes an outer element 110 with a permanent magnet 122. In other embodiments, the permanent magnet 122 may be, instead, one or more electromagnets and/or more than one permanent magnet. The inner element 120 includes a conductive winding 111 with a first coil 112a wound in one direction around the longitudinal axis and a second coil 112b wound in the opposite direction around the longitudinal axis.

As in the actuator 100 of FIG. 4, the coils 112a, 112b are of a width (in the longitudinal direction) such that the ends 124a, 124b of the permanent magnet lie within the width of the coils 112a, 112b.

As noted above, the actuator 100 of FIG. 4 and the actuator 310 of FIG. 7 are similar. In various embodiments, it may be advantageous to select an actuator embodiment in which the element including the coils is fixed and the element including the magnet moves. One potential advantage of such a selection is the simplification of electronic routing. For example, connecting the coils to a driver or a controller can be simplified if they are in a fixed position.

One potential advantage of the actuator 100 of FIG. 4 in which the coils 112a, 112b are placed on the outer element 100 is that heat generated by the current flowing through the coils 112a, 112b is more easily dissipated.

In the embodiment of FIG. 4, the conductive winding 111 includes two coils 112a, 112b. In an alternative embodiment, the conductive winding may include only one coil surrounding one end of the permanent magnet 122. One potential advantage of using two coils is to increase (in some instances double) the mechanical force generated from a single driven current. Another potential advantage of using two coils is to stabilize the inner element and restrict movement (translation or rotation) in directions other than along the longitudinal axis 10.

Figure 8:
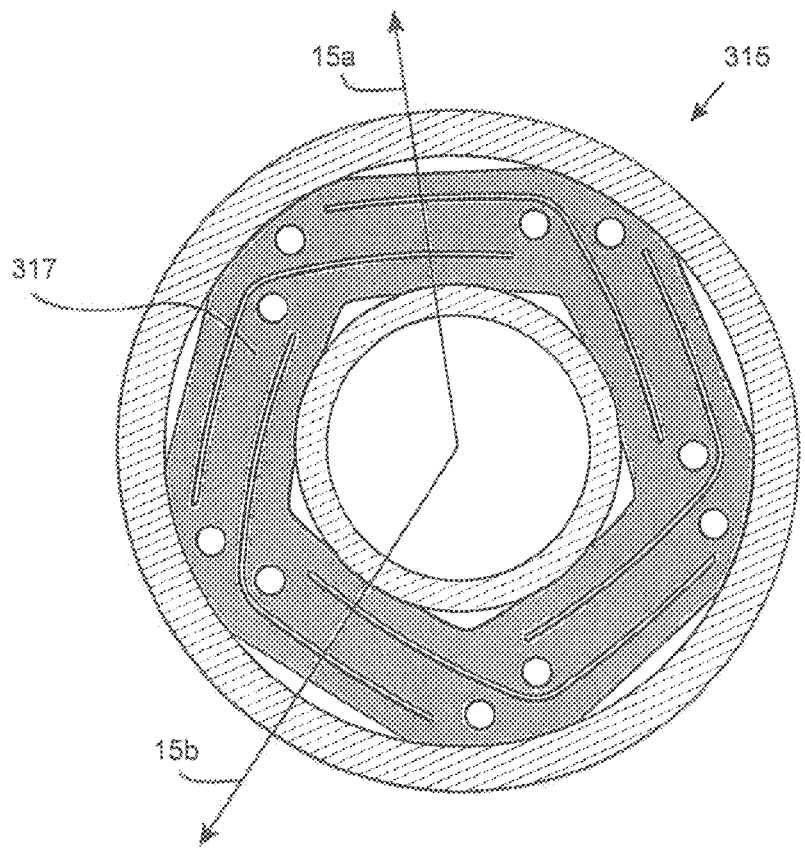
FIG. 8 illustrates an element coupling including five flexures arranged in a rotationally symmetric pattern.

As described above, the element coupling 115 of FIG. 3 includes three flexures 215 arranged in a rotationally symmetric pattern. FIG. 8 illustrates an element coupling 315 including five flexures 317 arranged in a rotationally symmetric pattern. It should be noted that FIG. 8 illustrates a plan view of the unflexed element coupling 315 whereas FIG. 3 is a perspective view of the flexed element coupling 115. As in the element coupling 115 of FIG. 3, the flexures 317 of the element coupling 315 of FIG. 8 are generally orthogonal to (1) the longitudinal axis (into and out of the page in FIG. 8) and (2) a radial axis 15a, 15b perpendicular to the longitudinal axis.

Whereas the element coupling 115 of FIG. 3 includes three flexures 215 and the element coupling 315 of FIG. 8 includes five flexures, it is to be appreciated that an element coupling may have any number of flexures arranged in the manner described above. An element coupling may have one flexure, two flexures, or more than two flexures. In some embodiments, the flexures do not surround the inner element joining.

Figure 9:
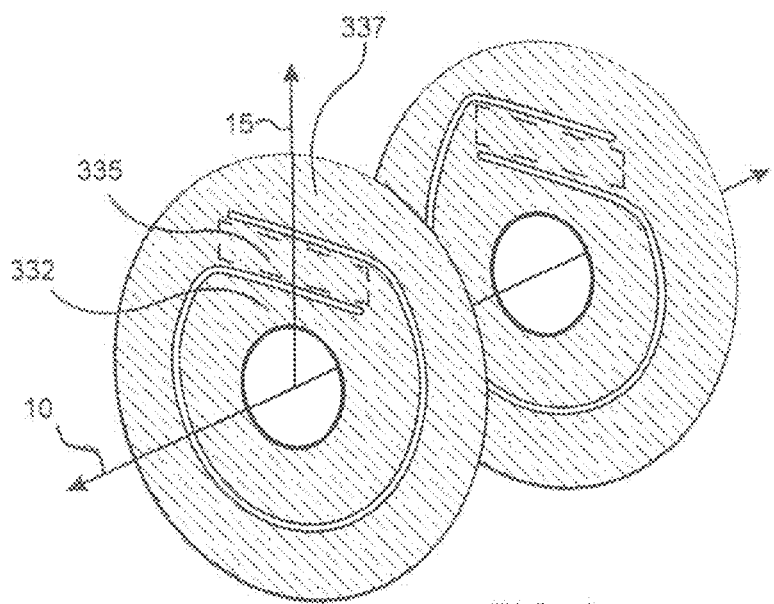
FIG. 9 illustrates an element coupling including a single flexure.

FIG. 9 illustrates an element coupling 325 including a single flexure. The element coupling includes an inner element region 332 coupled to an outer element region 337 by a single flexure 335. The flexure 335 is a strip of material generally orthogonal to (1) the longitudinal axis 10 and (2) a radial axis 15 perpendicular to the longitudinal axis.

In an embodiment of an actuator including two element couplings such as the element coupling 325 illustrated in FIG. 8, the element couplings 325, 327 may be disposed such that the rotational symmetries are in opposite directions (e.g., clockwise or counterclockwise) when viewed from the same end of the longitudinal axis.

Figures 10, 11:
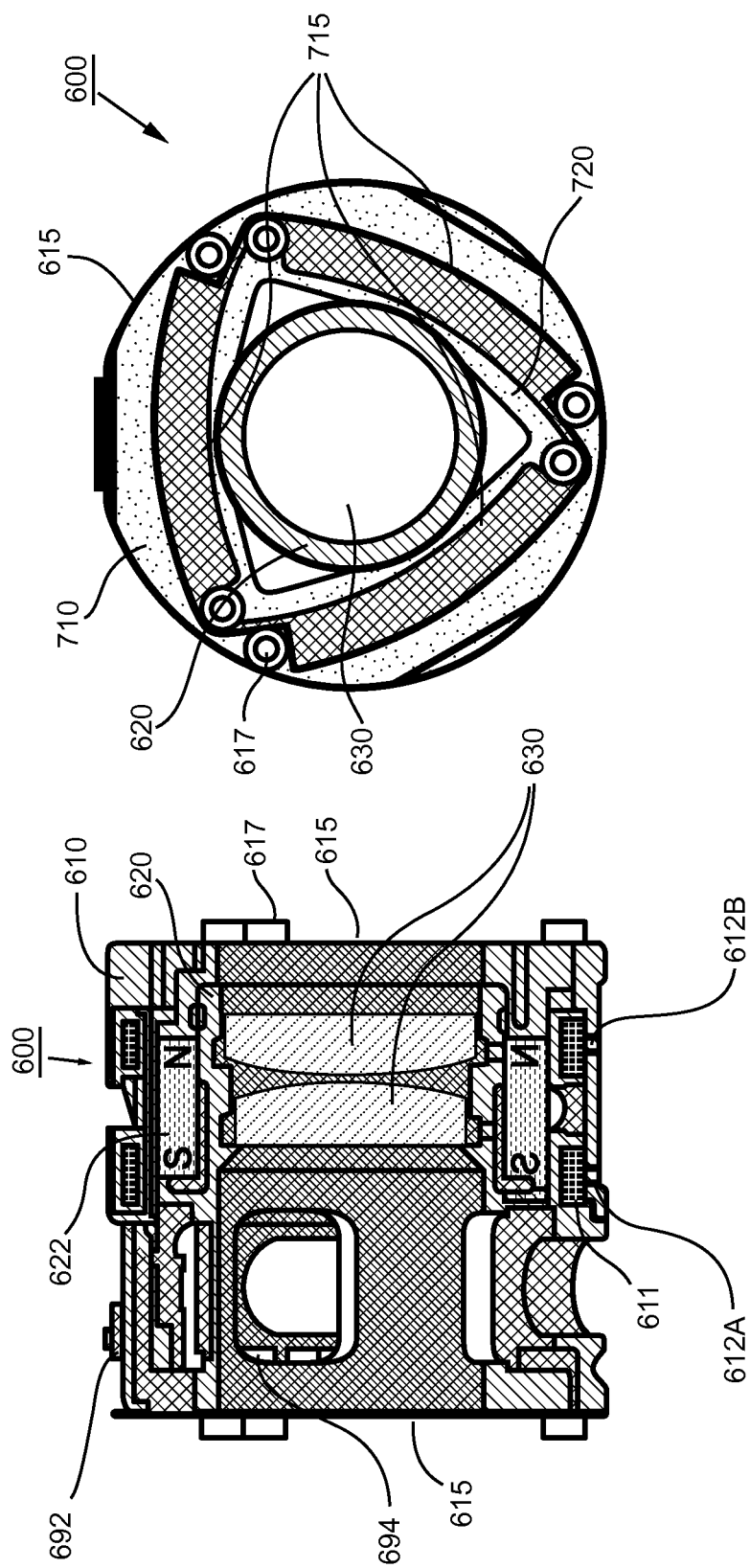
FIG. 10 illustrates a cross-sectional view of an actuator according to one embodiment.
FIG. 11 illustrates an axial view of the actuator of FIG. 10.

FIG. 10 illustrates a cross-sectional view of an actuator 600 according to one embodiment. FIG. 11 illustrates a side view of the actuator 600 of FIG. 10. The actuator 600 of FIG. 10 has a compact form factor and a high ratio of aperture diameter to total diameter. The actuator 600 is similar in many respects to and functions in much the same ways as the actuator 100 of FIG. 2, but differs in some respects as detailed below.

The actuator 600 includes an inner element 620 substantially housed by an outer element 610. The inner element 620 supports a lens assembly 630 (which in this case includes two optical glass lenses). The lens assembly 630 includes lenses of, for example, telecentric main confocal optics 42 of FIG. 1. The inner element 620 is coupled to the outer element 610 by two element couplings 615. The element couplings 615 are disposed at the longitudinal ends of the inner element 620 and outer element 610 (rather than between them as in the actuator 100 of FIG. 2). In particular, the actuator 200 includes a first element coupling 615 that couples a first end along the longitudinal axis of the inner element 620 to a first end along the longitudinal axis of the outer element 610 and a second element coupling 615 that couples second end along the longitudinal axis of the inner element 620 to a second end along the longitudinal axis of the outer element 610. This may increase the ratio of the aperture diameter to total diameter. The outer element may have a fixed position, and the inner element may be movable along a lens axis of the of the lens assembly 630.

The element couplings 615 include an outer element region 710 for coupling with the outer element 610 and an inner element region 720 for coupling with the inner element 610. The regions 710, 720 are joined by three flexures 715 arranged in a manner substantially similar to that described above with respect to the element coupling 115 of FIG. 3. The two element couplings 615 may act as a linear-motion bearing.

The two element couplings 615 may provide friction free movement between the inner element and the outer element. Additionally, changes in temperature do not cause the lens assembly 630 to lose alignment. In one embodiment, the two element couplings 615 act as a linear-motion bearing along a travel distance that is approximately 10% of a length of the flexures. In one embodiment, the length of the flexures is between approximately 20 and 40 millimeters.

The element couplings 615 are joined to the inner element 620 and outer element 610 by screws 617 which pass through holes in the element couplings (e.g., holes in the respective couplers 710, 720) and which secure the element couplings 615 with the respective element 610, 620. Alternatively, the regions 710, 720 may be secured to the inner element 620 and outer element 610 using glues or other adhesives, bolts, clasps, magnets, and so forth.

The inner element 620 of the actuator 600 includes a permanent magnet 622 and the outer element 610 includes a conductive winding 611 with a first coil 612a wound in a first direction around a first pole of the permanent magnet 622 and with a second coil 612b wound in a second direction around a second pole of the permanent magnet 622. The first coil 612a is in general registry (lateral overlap) with one of the magnetic poles of the permanent magnet 622, and the second coil 612b is in general registry (lateral overlap) with the other magnetic pole of the permanent magnet 622. The actuator 600 includes a linear encoder in the form of a sensor 692 mounted on the outer element 610 and a scale 694 mounted on the inner element 620.

Advantageously, the actuator 600 may be implemented in a small package with minimal weight. The actuator 600 may enable rapid changes in focus for a scanner that uses confocal microscopy. For example, in one embodiment, the actuator 600 may be moved at speed of approximately 60 millimeters per second or with an acceleration of up to seven g's (approximately 68.67 m/s$^2$). In particular, a current driven through the conductive winding 611 generates a magnetic field that interacts with the magnetic field generated by the permanent magnet to produce a force that moves the inner element 620 in the longitudinal direction with respect to the outer element 610 while the element couplings 615 prevent the inner element 620 from moving in other directions. Thus, the element couplings 615 may enable the inner element 620 to move along the axis of the lens assembly 630 in the inner element 620 to adjust the focus length of the lens assembly 630, while keeping the inner element 620 from shifting normal to the lens axis (e.g., while keeping the lens axis centered).

Figure 12:
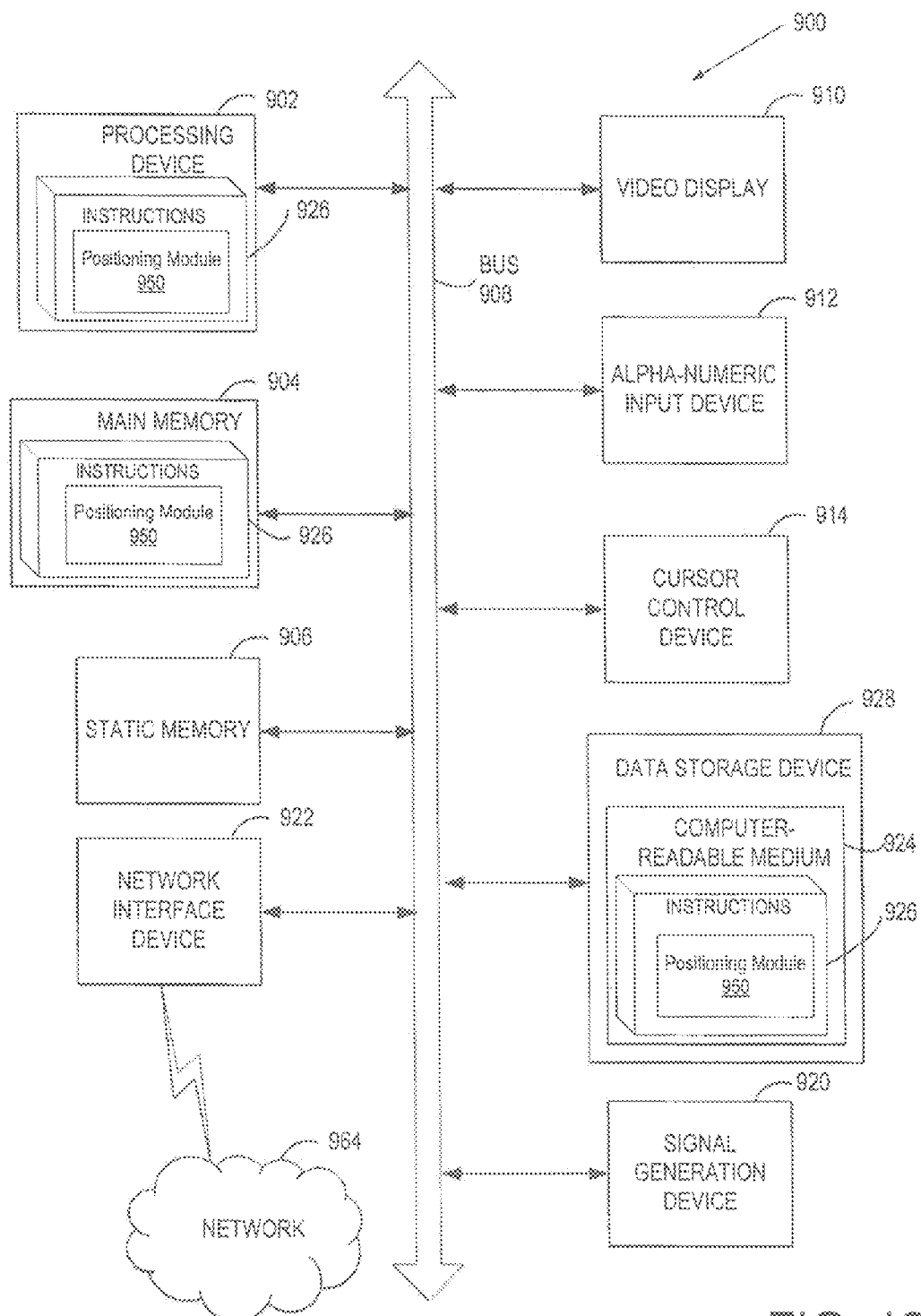
FIG. 12 illustrates a block diagram of an example computing device, in accordance with embodiments of the present invention.

FIG. 12 illustrates a diagrammatic representation of a machine in the example form of a computing device 900 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computing device 900 includes a processing device 902, a main memory 904 (e.g., read-only memory (ROM), flash memory, dynamic random access memory (DRAM) such as synchronous DRAM (SDRAM), etc.), a static memory 906 (e.g., flash memory, static random access memory (SRAM), etc.), and a secondary memory (e.g., a data storage device 928), which communicate with each other via a bus 908.

Processing device 902 represents one or more general-purpose processors such as a microprocessor, central processing unit, or the like. More particularly, the processing device 902 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 902 may also be one or more special-purpose processing devices such as an application specific integrated circuit (ASIC), a field programmable gate array (FPGA), a digital signal processor (DSP), network processor, or the like. Processing device 902 is configured to execute the processing logic (instructions 926) for performing operations and steps discussed herein.

The computing device 900 may further include a network interface device 922 for communicating with a network 964. The computing device 900 also may include a video display unit 910 (e.g., a liquid crystal display (LCD) or a cathode ray tube (CRT)), an alphanumeric input device 912 (e.g., a keyboard), a cursor control device 914 (e.g., a mouse), and a signal generation device 920 (e.g., a speaker).

The data storage device 928 may include a machine-readable storage medium (or more specifically a non-transitory computer-readable storage medium) 924 on which is stored one or more sets of instructions 926 embodying any one or more of the methodologies or functions described herein. Wherein a non-transitory storage medium refers to a storage medium other than a carrier wave. The instructions 926 may also reside, completely or at least partially, within the main memory 904 and/or within the processing device 902 during execution thereof by the computer device 900, the main memory 904 and the processing device 902 also constituting computer-readable storage media.

The computer-readable storage medium 924 may also be used to store a positioning module 950 to perform the functions of the controller 410 of FIG. 5, the method 500 of FIG. 6, or another function described here. The computer readable storage medium 924 may also store a software library containing methods that call the positioning module 950. While the computer-readable storage medium 924 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing or encoding a set of instructions for execution by the machine and that cause the machine to perform any one or more of the methodologies of the present invention. The term "computer-readable storage medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present invention have been described with reference to specific example embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense. The scope of the invention should, therefore, be determined with reference to the appended claims, along with the full scope of equivalents to which such claims are entitled.

What is claimed is:

1. A positioning system comprising:
    an actuator comprising:
        an inner element comprising a permanent magnet with a first pole and a second pole that define a magnetic axis parallel to a longitudinal axis;
        an outer element comprising a first coil wound in a first direction around the first pole and a second coil wound in a second direction around the second pole, wherein the outer element is coupled to a body of a scanner; and
        a linear-motion bearing that couples the inner element to the outer element, the linear-motion bearing providing a single degree of translational movement of the inner element with respect to the outer element along the longitudinal axis; and
    a controller to induce a current through the first coil and second coil to move the inner element with respect to the outer element along the longitudinal axis.

2. The positioning system of claim 1, further comprising:
    a lens assembly coupled to the inner element, the lens assembly having a lens axis that corresponds to the longitudinal axis, wherein movement of the inner element with respect to the outer element adjusts a focus of the lens assembly.

3. The positioning system of claim 1, wherein the inner element is concentric with the outer element.

4. The positioning system of claim 1, wherein the linear-motion bearing comprises a first element coupling that couples a first end along the longitudinal axis of the inner element to a first end along the longitudinal axis of the outer element and a second element coupling that couples a second end along the longitudinal axis of the inner element to a second end along the longitudinal axis of the outer element.

5. The positioning system of claim 4, wherein:
    the first element coupling comprises one or more first flexures that connect an inner element region of the first element coupling to an outer element region of the first element coupling, wherein the inner element region of the first element coupling connects to the inner element and the outer element region of the first element coupling connects to the outer element; and
    the second element coupling comprises one or more second flexures that connect an inner element region of the second element coupling to an outer element region of the second element coupling, wherein the inner element region of the second element coupling connects to the inner element and the outer element region of the second element coupling connects to the outer element.

6. The positioning system of claim 5, wherein the one or more first flexures comprises three flexures.

7. The positioning system of claim 5, wherein the one or more first flexures comprise one or more leaf springs.

8. The positioning system of claim 5, wherein the one or more first flexures generally encircle the inner element region.

9. The positioning system of claim 1, further comprising a linear encoder to measure a current position of the inner element with respect to the outer element, wherein the controller is to:
receive command data indicative of a desired position of the inner element with respect to the outer element;
receive position data from the linear encoder indicative of the current position of the inner element with respect to the outer element; and
induce the current based on the received command data and received position data.

10. A device comprising:
an outer element;
an inner element disposed within the outer element, the inner element comprising a lens assembly having a lens axis; and
a linear-motion bearing that couples the inner element to the outer element, the linear-motion bearing providing a single degree of translational movement of the inner element along the lens axis, the linear-motion bearing comprising:
a first element coupling comprising a first inner element region coupled to the inner element, a first outer element region coupled to the outer element, and one or more first flexures that connect the first inner element region to the first outer element region of the first element coupling; and
a second element coupling comprising a second inner element region coupled to the inner element, a second outer element region coupled to the outer element, and one or more second flexures that connect the second inner element region to the second outer element region of the second element coupling, wherein the first inner element region and second inner element region rotate in a same direction as the inner element is moved along the lens axis.

11. The device of claim 10, wherein the first element coupling is coupled to a first end of the inner element and a first end of the outer element along the lens axis and the second element coupling is coupled to a second end of the inner element and a second end of the outer element along the lens axis.

12. The device of claim 10, wherein the one or more first flexures bend as the inner element is moved along the lens axis with respect to the outer element.

13. The device of claim 10, wherein the one or more first flexures comprises at least three flexures, and the first element coupling comprises a homogenous material.

14. The device of claim 10, wherein the first inner element region, the first outer element region, the inner element, the outer element and the lens assembly are all approximately concentric.

15. An apparatus comprising:
an outer element having a first end and a second end along a longitudinal axis;
an inner element disposed within the outer element, the inner element having a first end and a second end along the longitudinal axis;
a first element coupling comprising a first outer element region attached to the first end of the outer element, a first inner element region attached to the first end of the inner element, and three or more first flexures, wherein each of the three or more first flexures is a strip of material that is connected at one end to the first outer element region and at an opposite end to the first inner element region and that is generally perpendicular to a radial axis radiating from the longitudinal axis, and wherein the three or more first flexures generally circumscribe the first inner element region; and
a second element coupling comprising a second outer element region attached to the second end of the outer element, a second inner element region attached to the second end of the inner element, and three or more second flexures, wherein each of the three or more second flexures is a strip of material that is connected at one end to the second outer element region and at an opposite end to the second inner element region and that is generally perpendicular to a radial axis radiating from the longitudinal axis, and wherein the three or more second flexures generally circumscribe the second inner element region.

16. The apparatus of claim 15, wherein each of the three or more first flexures and each of the three or more second flexures is curved or straight.

17. The apparatus of claim 15, further comprising:
a lens assembly coupled to the inner element, the lens assembly having a lens axis that corresponds to the longitudinal axis, wherein movement of the inner element with respect to the outer element adjusts a focus of the lens assembly.

18. The apparatus of claim 15, wherein the three or more first flexures comprise three or more leaf springs.

19. The apparatus of claim 15, wherein:
the inner element comprises a permanent magnet with a first pole and a second pole that define a magnetic axis parallel to the longitudinal axis;
the outer element comprises a first coil wound in a first direction around the first pole and a second coil wound in a second direction around the second pole; and
the apparatus further comprises a controller to induce current through the first coil and the second coil to move the inner element with respect to the outer element along the longitudinal axis.

20. The apparatus of claim 19, further comprising a linear encoder to measure a current position of the inner element with respect to the outer element, wherein the controller is to:
receive command data indicative of a desired position of the inner element with respect to the outer element;
receive position data from the linear encoder indicative of the current position of the inner element with respect to the outer element; and
induce the current based on the received command data and received position data.

21. A positioning system comprising:
an actuator comprising:
an inner element comprising a permanent magnet with a first pole and a second pole that define a magnetic axis parallel to a longitudinal axis;
an outer element comprising a first coil wound in a first direction around the first pole and a second coil wound in a second direction around the second pole; and
a linear-motion bearing that couples the inner element to the outer element, the linear-motion bearing providing a single degree of translational movement of the inner element with respect to the outer element along the longitudinal axis, wherein the linear-motion bearing comprises one or more first leaf springs that couple a first end along the longitudinal axis of the inner element to a first end along the longitudinal axis of the outer element and one or more second leaf springs that couple a second end along the longitudinal axis of the inner element to a second end along the longitudinal axis of the outer element; and a controller to induce a current through the first coil and second coil to move the inner element with respect to the outer element along the longitudinal axis.

22. The positioning system of claim 21, further comprising:
a lens assembly coupled to the inner element, the lens assembly having a lens axis that corresponds to the longitudinal axis, wherein movement of the inner element with respect to the outer element adjusts a focus of the lens assembly.

23. The positioning system of claim 21, wherein the inner element is concentric with the outer element.

24. The positioning system of claim 21, wherein the one or more first leaf springs generally encircle the inner element.

25. The positioning system of claim 21, further comprising a linear encoder to measure a current position of the inner element with respect to the outer element, wherein the controller is to:
receive command data indicative of a desired position of the inner element with respect to the outer element;
receive position data from the linear encoder indicative of the current position of the inner element with respect to the outer element; and
induce the current based on the received command data and received position data.

26. A device comprising:
an outer element;
an inner element disposed within the outer element, the inner element comprising a lens assembly having a lens axis; and
a linear-motion bearing that couples the inner element to the outer element, the linear-motion bearing providing a single degree of translational movement of the inner element along the lens axis, the linear-motion bearing comprising at least a first element coupling comprising:
a first inner element region coupled to the inner element;
a first outer element region coupled to the outer element; and
at least three flexures that connect the first inner element region to the first outer element region of the first element coupling, wherein the first element coupling comprises a homogenous material.

27. The device of claim 26, wherein the first element coupling is coupled to a first end of the inner element and a first end of the outer element along the lens axis and a second element coupling is coupled to a second end of the inner element and a second end of the outer element along the lens axis.

28. The device of claim 27, wherein the first inner element region, the first outer element region, the inner element, the outer element and the lens assembly are all approximately concentric.

29. The device of claim 26, wherein the at least three flexures bend as the inner element is moved along the lens axis with respect to the outer element.

* * * * *